United States Patent
Canty et al.

(10) Patent No.: US 10,577,877 B2
(45) Date of Patent: Mar. 3, 2020

(54) MUD FLOW MONITORING DEVICES AND METHODS

(71) Applicant: J. M. Canty, Inc., Buffalo, NY (US)

(72) Inventors: Thomas M. Canty, Williamsville, NY (US); Miles Priore, Williamsville, NY (US); Colin Dalton, Dublin (IE)

(73) Assignee: J.M. CANTY, INC, Buffalo, NY (US)

( * ) Notice: Subject to any disclaimer, the term of this patent is extended or adjusted under 35 U.S.C. 154(b) by 40 days.

(21) Appl. No.: 15/668,717

(22) Filed: Aug. 4, 2017

(65) Prior Publication Data

US 2018/0038179 A1 Feb. 8, 2018

Related U.S. Application Data

(60) Provisional application No. 62/370,752, filed on Aug. 4, 2016.

(51) Int. Cl.
 *E21B 21/08* (2006.01)
 *G06T 7/246* (2017.01)
 (Continued)

(52) U.S. Cl.
 CPC ............ *E21B 21/08* (2013.01); *E21B 47/042* (2013.01); *G01F 1/7086* (2013.01); *G06T 7/248* (2017.01);
 (Continued)

(58) Field of Classification Search
 CPC ........ E21B 21/08; E21B 47/042; E21B 47/10; G01N 21/15; G06K 9/00771; G06T 2207/30181; G06T 7/248
 See application file for complete search history.

(56) References Cited

U.S. PATENT DOCUMENTS 2,667,109 A * 1/1954 Piety .................... G03B 37/005
 396/19
3,256,936 A * 6/1966 Johnson ................. E21B 7/12
 166/354
(Continued)

FOREIGN PATENT DOCUMENTS

EP 1406079 A2 4/2004
WO 2016007139 A1 1/2016

OTHER PUBLICATIONS

Canty Process Technology, "vision without limits: Oil & Gas, Exploration & Production", pp. 1-12, Jul. 2017.
(Continued)

*Primary Examiner* — Md N Haque
(74) *Attorney, Agent, or Firm* — Leydig, Voit & Mayer, Ltd.

(57) ABSTRACT

A flow monitoring device for monitoring mud flow in a return line of a bore hole drilling operation, including a mounting bracket mounted to the return line with a viewing port for access to an interior of the return line. A light source illuminates, through the viewing port, a portion of the mud flow in an observation zone within the return line. A camera creates a plurality of images of the mud flow in the observation zone. A controller is configured to analyze the plurality images to: determine a level of the mud flow in the return line and the presence of at least one irregularity, track a movement of the irregularity across the plurality of images to determine a rate of movement of the irregularity, and calculate a flow rate of the mud flow through the return line based on the movement rate and the determined level.

16 Claims, 11 Drawing Sheets

(51) Int. Cl.
*E21B 47/04* (2012.01)
*G01F 1/708* (2006.01)
*G06K 9/00* (2006.01)
*G06K 9/20* (2006.01)
*H04N 5/225* (2006.01)

(52) U.S. Cl.
CPC ....... *G06K 9/00771* (2013.01); *G06K 9/2027* (2013.01); *G06T 2207/10016* (2013.01); *G06T 2207/30181* (2013.01); *H04N 5/2252* (2013.01)

(56) References Cited

U.S. PATENT DOCUMENTS

| | | | |
|---|---|---|---|
| 5,230,556 A | 7/1993 | Canty et al. | |
| 5,502,686 A * | 3/1996 | Dory | G01V 11/00 367/34 |
| 2011/0240134 A1 * | 10/2011 | O'Brien | F16K 37/0058 137/15.01 |
| 2014/0250987 A1 * | 9/2014 | Canty | G01N 1/38 73/64.56 |
| 2015/0007983 A1 * | 1/2015 | Tjhang | E21B 47/0002 166/250.01 |
| 2016/0216213 A1 | 7/2016 | O'Brien et al. | |

OTHER PUBLICATIONS

Canty Process Technology, "Mud Flow and Quality Analyzer", pp. 1-2, Dec. 2010.

\* cited by examiner

MUD FLOW MONITORING DEVICES AND METHODS

CROSS-REFERENCE TO RELATED APPLICATIONS

This application claims benefit of U.S. Provisional Patent Application No. 62/370,752, which was filed on Aug. 4, 2016.

FIELD OF THE DISCLOSURE

The present disclosure relates to an apparatus for use in a system for drilling a subterranean bore hole, particularly but not exclusively an oil, gas or geothermal well.

BACKGROUND OF THE INVENTION

The system, devices, and methods under consideration relate to the drilling of a bore hole or well typically carried out using a steel pipe known as a drill string with a drill bit on the lowermost end. The entire drill string may be rotated using an over-ground drilling motor or the drill bit may be rotated independently of the drill string using a fluid powered motor or motors mounted in the drill string just above the drill bit. As drilling progresses, a flow of mud is used to carry the debris created by the drilling process out of the bore hole. Mud is pumped through an inlet line down the drill string to pass through the drill bit and returns to the surface via an annular space between the outer diameter of the drill string and the bore hole. Mud is a very broad drilling term, and in this context it is used to describe any fluid or fluid mixture used during drilling.

When drilling for oil or gas or other objectives, the drilling mud is used to lubricate the drill bit and pull cuttings up through the annular space. The mud and cuttings exit the well and are typically directed to a shaker to screen out the cuttings, and then to a further treatment step before the mud, minus contaminants, is returned to the bore hole. It is well known to monitor the flow of mud through the drilling system because it is important to the proper functioning of the drill bit and because unexpected changes in mud flow may indicate potentially dangerous conditions.

Current technologies that monitor mud flow have deficiencies. For example, Coriolis meters are unable to detect a stoppage of mud flow and have limitations related to reliability. Deflecting paddle systems have poor resolution and wear out quickly due to the abrasive quality of the mud and cuttings.

SUMMARY OF THE DISCLOSURE

In one aspect, the disclosure describes a flow monitoring device for monitoring mud flow in a return line of a bore hole drilling operation, including a mounting bracket mounted to the return line with a viewing port for access to an interior of the return line. A light source illuminates, through the viewing port, a portion of the mud flow in an observation zone within the return line. A camera creates a plurality of images of the mud flow in the observation zone. A controller is configured to analyze the plurality images to: determine a level of the mud flow in the return line and the presence of at least one irregularity, track a movement of the irregularity across the plurality of images to determine a rate of movement of the irregularity, and calculate a flow rate of the mud flow through the return line based on the movement rate and the determined level.

In another aspect, the disclosure describes a method of monitoring mud flow in a return line of a bore hole drilling operation, including: illuminating an observation zone in the interior of the return line; creating a plurality of images of the mud flow in the observation zone of the return line; detecting an edge of the mud flow so as to determine a level of the mud flow in the return line; detecting an irregularity in the mud flow and tracking movement of the irregularity over the plurality of images so as to determine a velocity of the mud flow in the return line; and calculating a volume flow rate of the mud flow based on the determined level and determined velocity.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims. The terms configured and configuration as used herein refer to a specified structural size and shape.

Figure 1:
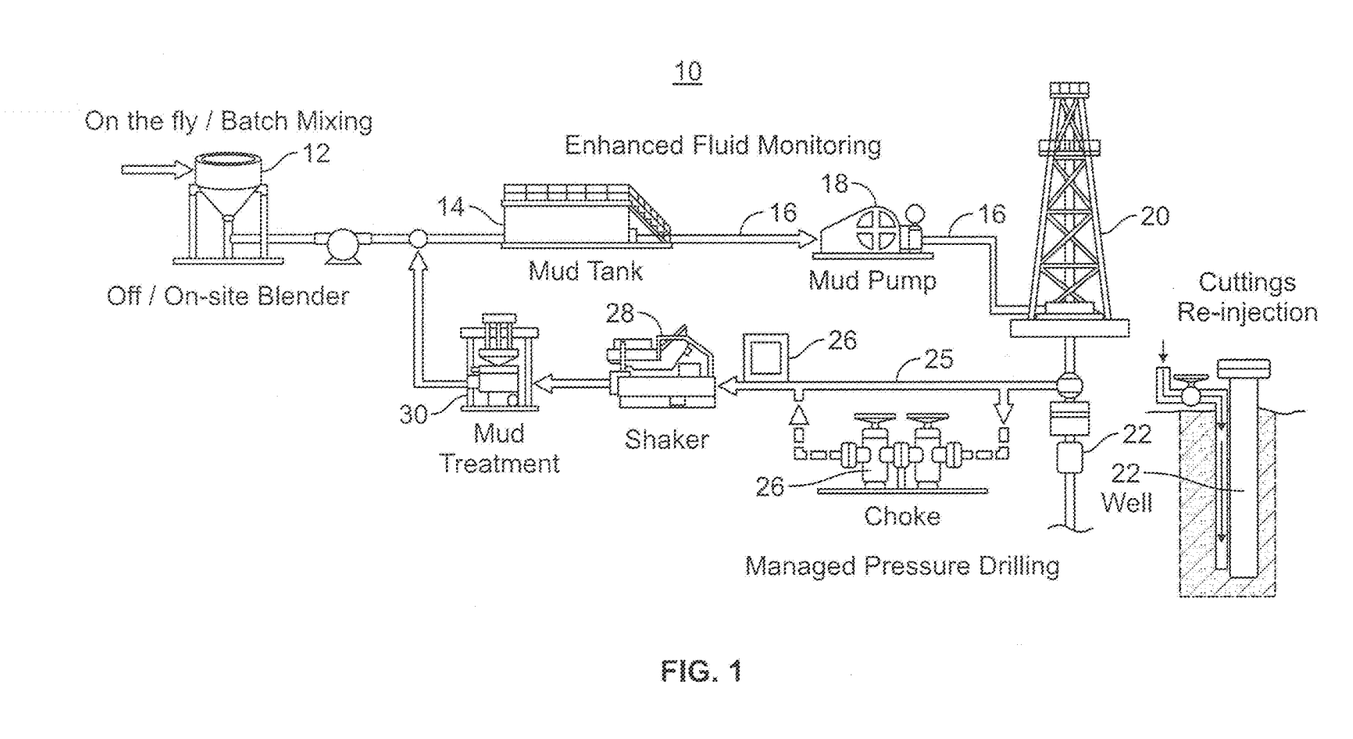
FIG. 1 is a diagrammatic view of a drilling system incorporating a flow monitoring device.

Reference is made to FIG. 1, which generally illustrates the setting in which mud flow monitoring devices according to embodiments of the disclosure will operate and some of the main elements of a drilling operation 10. The drilling operation 10 includes a mud preparation system 12, which may be on the drilling site or remote from the drill site. The mud preparation system 12 is where the mud is prepared. The mud from the mud preparation system 12 may be supplied to a mud tank 14 via pipes, for example, and stored within the mud tank. Mud from the mud tank 14 is moved through mud supply pipes 16 with a mud pump 18 to a drilling operation 20. The drilling operation 20 includes conventional well drilling elements, such as a drill string and drill bit 22. Mud is supplied to the drill string and bit 22 as is well known to lubricate the drill bit and provide a carrier for the removal of drilling cuttings.

Mud and cuttings may be conveyed from the drilling operation 20 through a return pipe or line 25 to a choke 24 and past a mud flow monitoring device 26 according to the present disclosure. The return line 25 is typically angled or tilted downwardly along the longitudinal axis thereof in the flow direction so that gravity assists in moving the mud through the pipe past the mud flow monitoring device 26. In general, the mud flow monitoring device 26 is used to monitor the flow of mud from the drilling operation and provides an indication of the volume of mud flow past the device over time. The rate of flow information thus acquired can be used to detect flow spikes and/or losses and other flow conditions. For example, if the mud flow monitoring device 26 detects mud flow when there is no active pumping, an imbalance in the mud pressure vs the formation pressure may exist, and a blowout of the well may occur. In another example, the mud flow monitoring device 26 may be employed during pressure testing of the well 22. The well 22 is sealed off when it is desired to determine the well pressure and calculate the mud density needed to control the well. If the well seal leaks or there is a bypass, mud flow would be detected by the mud flow monitoring device 26.

Mud and cuttings 56 passing by or through the mud flow monitoring device 26 are delivered to a conventional shaker 28 and other conventional mud treatment devices 30 where mud is separated from the cuttings and other contaminants. The separated mud can be returned to the mud tank 14 for storage and reuse. The cuttings and other contaminants may be further processed and/or disposed of as is well known.

Referring to FIGS. 2-7, a mud flow monitoring device 26 according to one embodiment of the disclosure is illustrated. Among the principal elements of the mud flow monitoring device 26 is a bracket 32 or framework that is configured for attachment to the return line 25 (FIG. 1). The mud flow monitoring device 26 includes an light source 42, an camera 44, a controller 46, and a power supply 48 mounted to the bracket 32. An actuator module 54 is provided to supply cleaning fluid to the camera 44.

Figure 2:
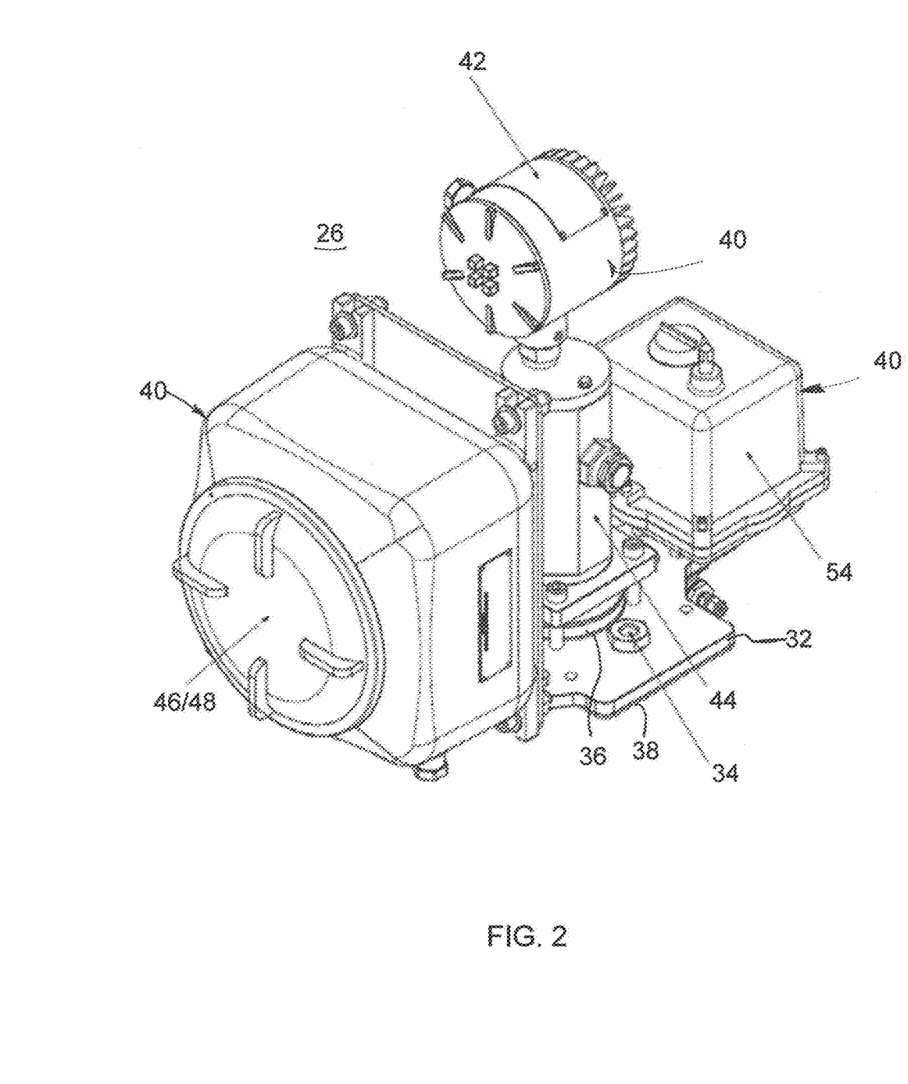
FIG. 2 is a perspective view of a mud flow monitoring device according to one embodiment of the disclosure

The bracket 32 may be a single, unitary piece, or may be an assembly of individual joined pieces. The pieces may be joined by welding or with conventional fasteners. The bracket 32 may be made of any suitable material that is sufficiently strong and robust to support and protect the elements of the mud flow monitoring device 26 in what is considered a harsh operational environment, such as steel.

The bracket 32 may include a first port 34 for access to the interior of the return line 25, when the bracket is attached thereto. The first port 34 may be used by an operator to inspect the interior of the return line and for the insertion of instruments to calibrate the mud flow monitoring device 26 as well as other devices as will be detailed herein.

Calibration of the device 26 may involve the location of the bottom dead center (BDC) of the return line 25. To determine the BDC, an operator may run a low level (for example, approximately ½" deep) stream of water or mud through the return line 25 and the mud flow monitoring device 26 detects both sides of the stream and thus determines the center of the stream. The center of the calibration stream establishes where the BCD of the return line 25 is located. A mathematical calculation may be performed to determine how full the return line 25 is according to the detected position of the fluid level along the wall of the return line, which then enables the calculation of the volume flow rate by fluid mechanics open channel flow calculations using the height of the fluid and the angle of the return line or other calculations.

Figure 7:
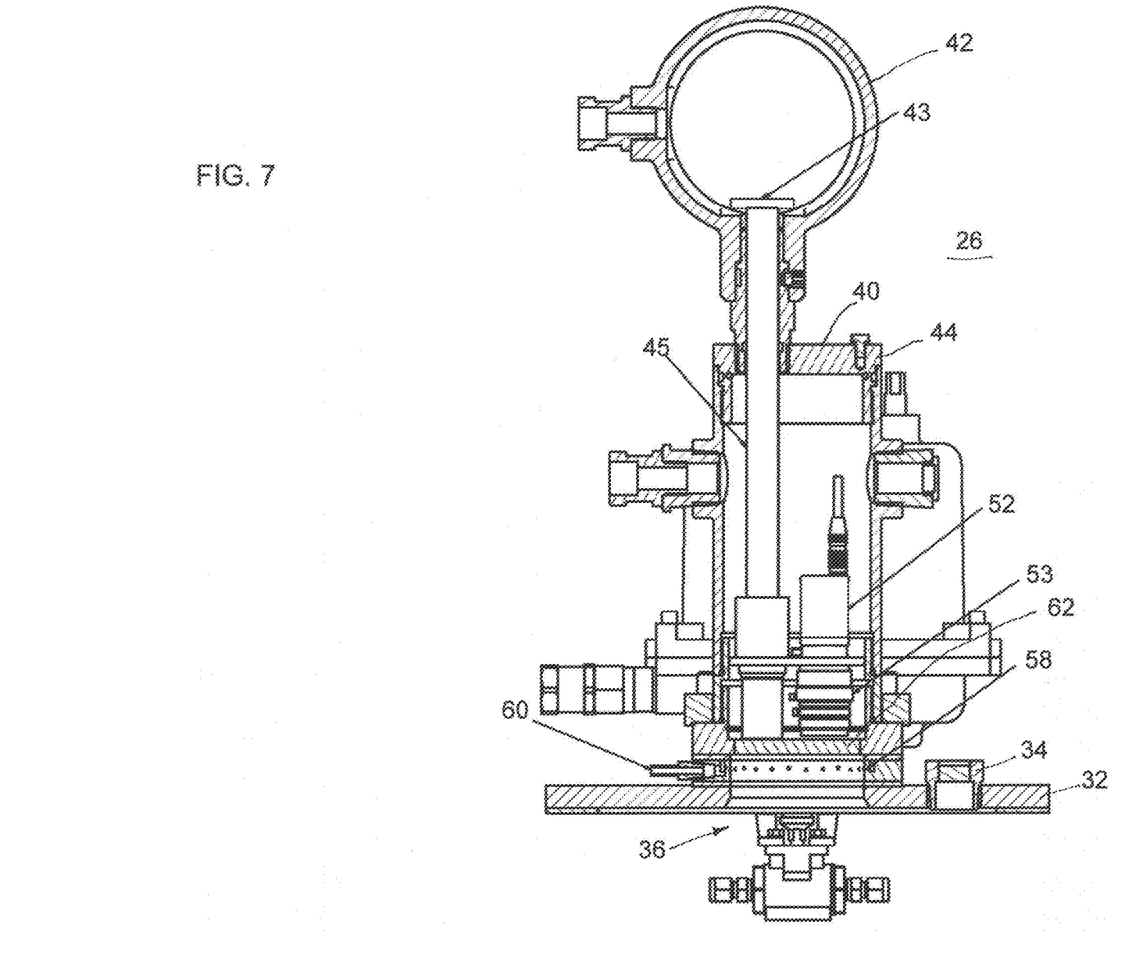
FIG. 7 is a cross section view of the mud flow monitoring device of FIG. 2 illustrating an light source, an camera, and a spray ring.

A second port 36 is provided in a base portion 38 of the bracket 32. The second port 36 is sized to provide a viewing opening through which the mud flow monitoring device 26 optically monitors the fluid level and velocity of the mud moving through the return line 25. The second port 36 aligns with a corresponding opening (not shown) in the return line 25 when mounted thereto. The second port 36 may be provided with a transparent window 62 (FIG. 7).

A housing 40 is attached to the bracket 32 for enclosing elements of the mud flow monitoring device 26. The housing 40 may include one housing enclosure or a plurality of separate housing enclosures. The housing 40 may be constructed of steel or any suitably robust material for protecting the operating elements of the mud flow monitoring device 26. The housing 40 may be explosion-proof. In an alternate embodiment, the housing 40 and bracket 32 may be combined and attached directly to the line 25.

The light source 42 may include any controllable light source that can be operated to illuminate the interior of the 25 return line adjacent the mud flow monitoring device 26 in a zone of the return line that shall be referred to as the observation zone 50. The observation zone 50 is the area adjacent the mud flow monitoring device 26 that is sized and shaped to be illuminated by the light source 42 and optically observable by the camera 44.

Figure 9:
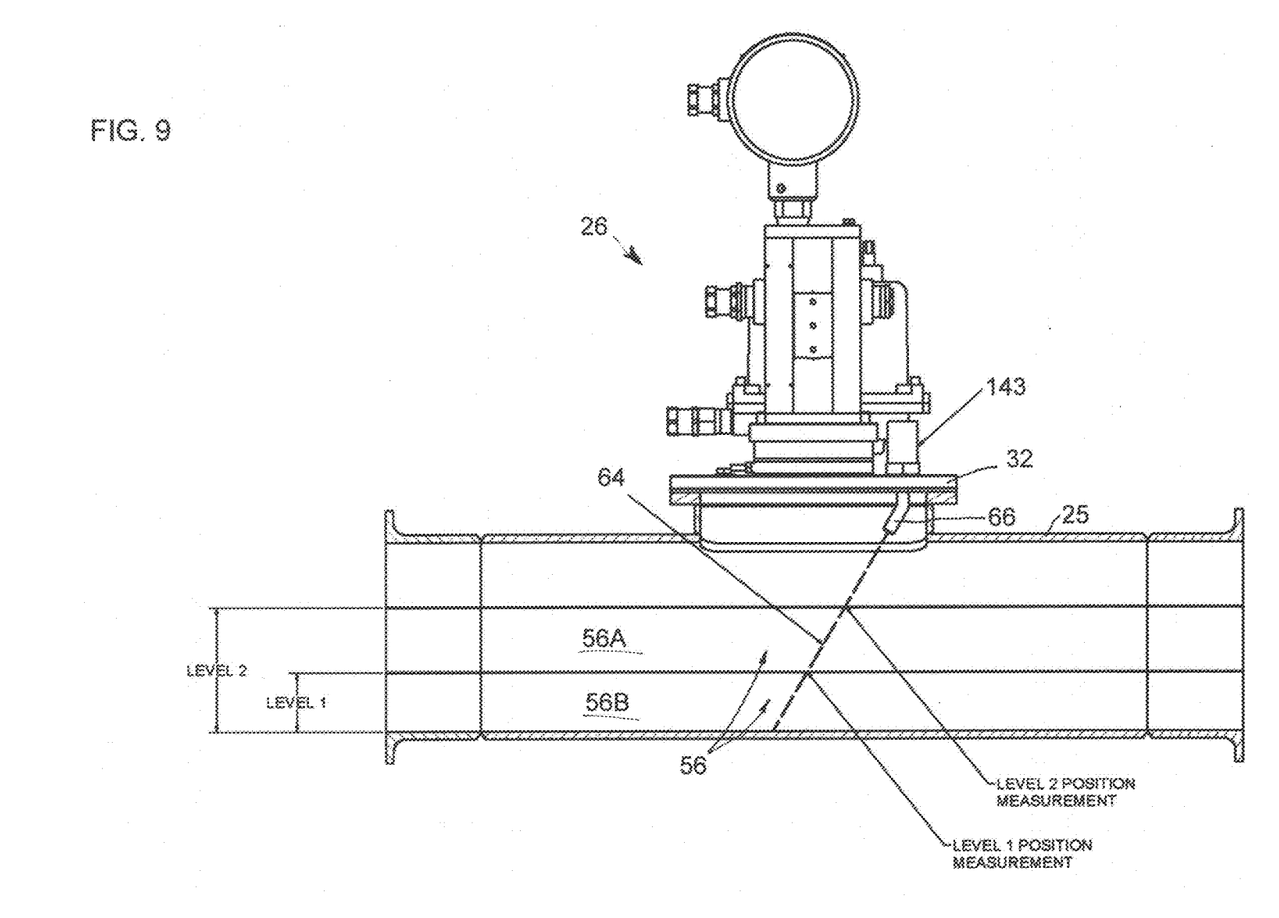
FIG. 9 is a side view of another embodiment of a mud flow monitoring device with an alternative laser light source and configuration.
Figure 11:
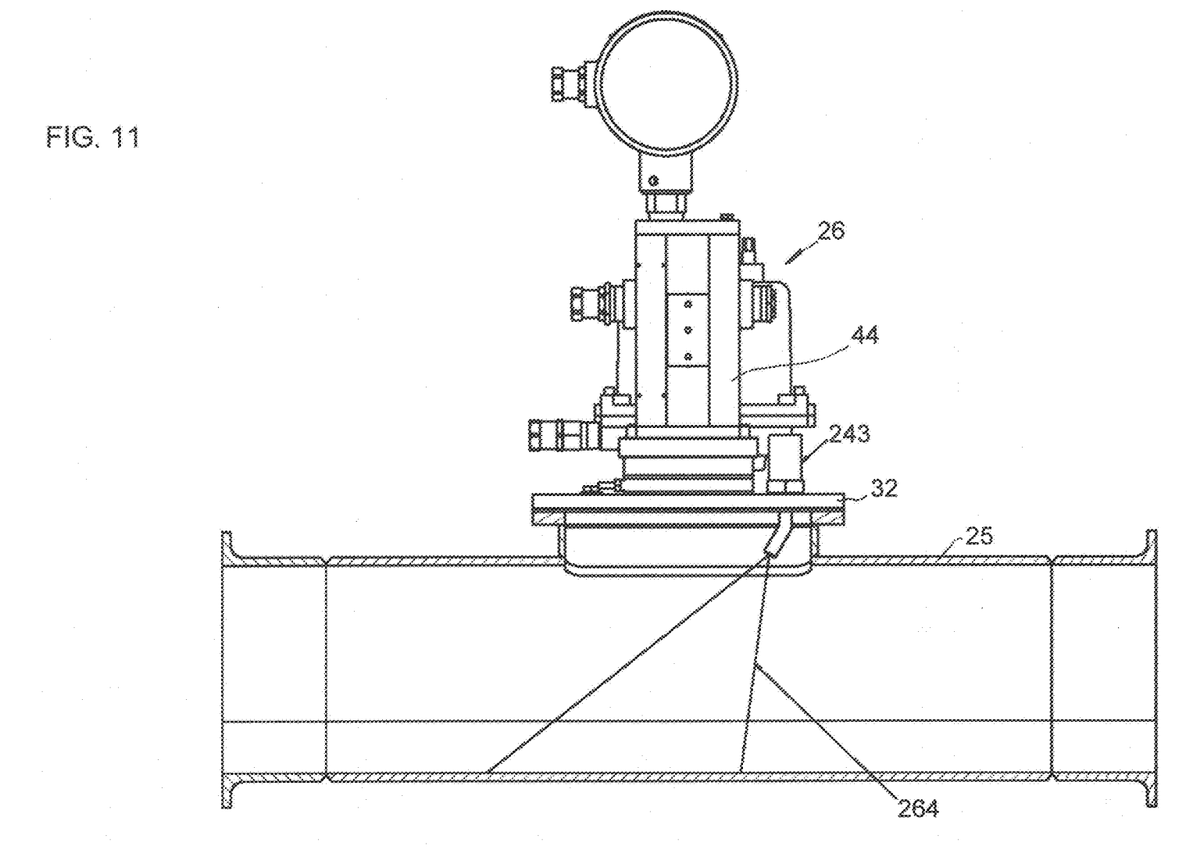
FIG. 11 is a side view of yet another embodiment of a mud flow monitoring device with an alternative UV light source and configuration.

For example, the light source 42 may be or may include an electrically powered light 43. The light 43 can be activated and deactivated at high speeds. Alternatively, the light 43 of the light source 42 may be powered on without interruption during operation of the mud flow monitoring device 26. Examples of such devices include electroluminescent devices, such as light emitting diodes as shown in FIG. 7, lasers as shown in FIG. 9, or an ultraviolet (UV) light source as shown in FIG. 11. Alternatively, the light source 42 could be any suitable light source, such as an white light lamp, halogen light, or LEP.

The controller 46 is operable to activate and deactivate the light source 42 so as to illuminate the fluid in the observation zone 50 in a desired manner, and may include components for operating the light source in a specialized manner, such as a strobe generator. The light source 42 may include a light guide 45 to direct light generated by the light 43 through the housing 40 of the camera 44, through the second port 36, which is provided with a transparent window 62 (FIG. 7) and into the interior of the return line 25. The window 62 isolates the elements of the mud flow monitoring device 26 from the contents of the return line 25.

The camera 44 includes an imaging device 52, such as a digital camera, with a lens 53 that is configured to focus at the distances and angles required. The camera can be any appropriate device for capturing images of the fluid within the observation zone 50, including a still digital camera or a video camera.

Other methods of obtaining image data of the mud flow in the observation zone 50 are also possible, for example, using magnetic imaging, sonar, radar, or any other means to determine characteristics of the flow within observation zone 50. Any device capable of obtaining such image data should also be considered an imaging device 52 within the meaning of the present description.

As shown in FIG. 7, a spray ring 58 may be arranged at the window 62 disposed adjacent the second port 36. The spray ring 58 is configured to spray cleaning fluid on the window 62 side that is facing the observation zone 50. Spray rings are known in other imaging systems, the details of which may be gleaned from U.S. Pat. No. 6,359,742, for example. The spray ring 58 is supplied with cleaning fluid by a spray inlet 60 in communication with the spray ring. The spray inlet 60 may be opened and closed by actuator module 54. The spray inlet 60 and ring 58 is configured to supply cleaning fluid to the window 62 on a scheduled basis or when the window is occluded with contaminants, such as mud or constituents of the mud returning from the well 22. The mud flow monitoring device 26 may be configured to detect that the window 62 is occluded when it is not possible to resolve the inside of the return line 25, which signals the actuator to open the spray inlet 60, causing the spray ring 58 to direct cleaning fluid, for example water, onto the window until the window is determined to be cleared of occluding materials.

In the illustrated embodiment, an imaging controller and computational unit may both be integrated into a controller 46 that both operates the light source 42, camera 44, and optionally the actuator 54 and performs computations to analyze the images acquired by the imaging device 52 in order to generate analytical data about the fluid flow within the observation zone 50 of the return line 25.

The controller 46 computes analytical data associated with the flow of fluid passing through the return line 25 in the observation zone 50. In the illustrated embodiment, the control system 46 is housed with the power supply 48. However, it is also possible for the control system 46 to be consolidated into a single unit, or to be spread over additional modules that perform discrete tasks. The control system 46, preferably includes at least one electronic controller that operates in a logical fashion to perform operations, execute control algorithms, store and retrieve data and other desired operations. These controllers may include or access memory, secondary storage devices, processors, and any other components for running applications. The memory and secondary storage devices may be in the form of read-only memory (ROM) or random access memory (RAM) or integrated circuitry that is accessible by the controller. Various other circuits may be associated with the control system such as power supply circuitry, signal conditioning circuitry, driver circuitry, and other types of circuitry. The term "controller" is meant to be used in its broadest sense to include one or more controllers and/or microprocessors that may be associated with the control system and that may cooperate in controlling various functions and operations of the components of the the mud flow monitoring device 26. The functionality of the controller 46 may be implemented in hardware and/or software without regard to the functionality.

In operation, the computational unit receives image data from the camera 44 and uses algorithms to analyze the images for determining certain characteristics of the flow, such as particle or bubble velocity and the angle of the edge of the flow material, such as the meniscus of the flow material. As a result of analyzing the images, the computational unit produces analytical data that includes at least one measure of a determined flow characteristic, such as velocity, volume or volume flow rate data. Once the analytical data has been determined by the computational unit of the controller 46, the image data can be deleted or stored.

Having established the BDC of the return line 25, determining the volumetric flow rate of mud in the pipe is then a matter of detecting the edge (e.g., the meniscus) of a mud flow 56 through the return line, determining the angle of the edge, and calculating the cross sectional area of mud in the pipe 25 at a given time. When a feature is detected in the mud flow 56, such as a bubble, particle, foam, or other irregularity, the feature is followed or tracked in the images acquired by the camera 44 over time. Movement of the feature is used to calculate the velocity of the mud flow 56. The velocity and volume of mud flow 56 through the return line 25 then yields the volume flow rate.

The volume flow rate can be used by operators to determine several aspects of the drilling system 10. A difference between the volume flow rate of mud entering the system and that volume flow rate detected by the mud flow monitoring device 26 can indicate a problem. For example, if the volume flow rate detected by the mud flow monitoring device 26 is lower than that pumped into the well 22, a dangerous overpressure condition may be indicated, and the operator may shut the system down to avoid damage to equipment. The controller 46 may also recognize foam and may be configured to calculate how much foam is present in the mud flow. Presence of a large amount of foam will allow the control of the use of anti-foam or indicate a possible gas kick.

Figure 3:
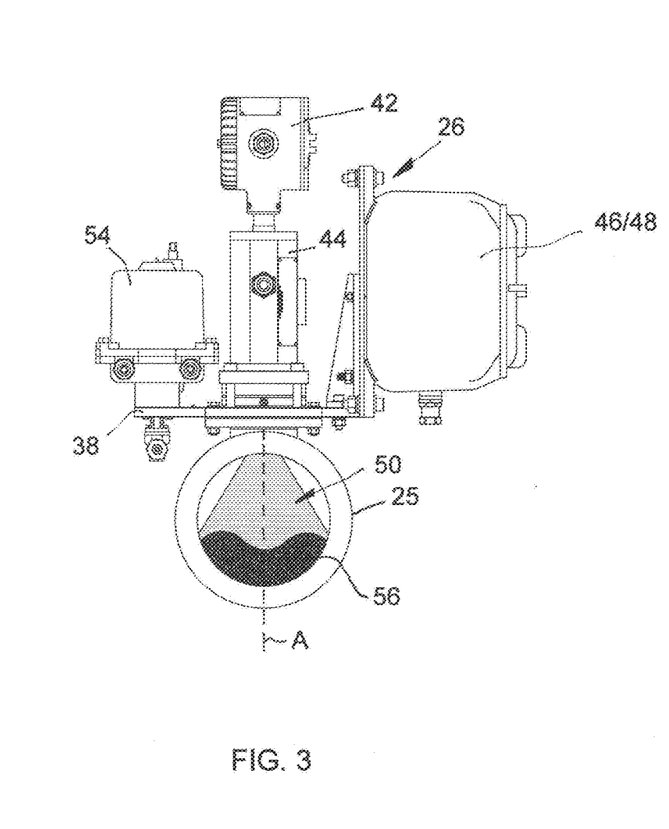
FIG. 3 is a front view of the mud flow monitoring device of FIG. 2.
Figure 4:
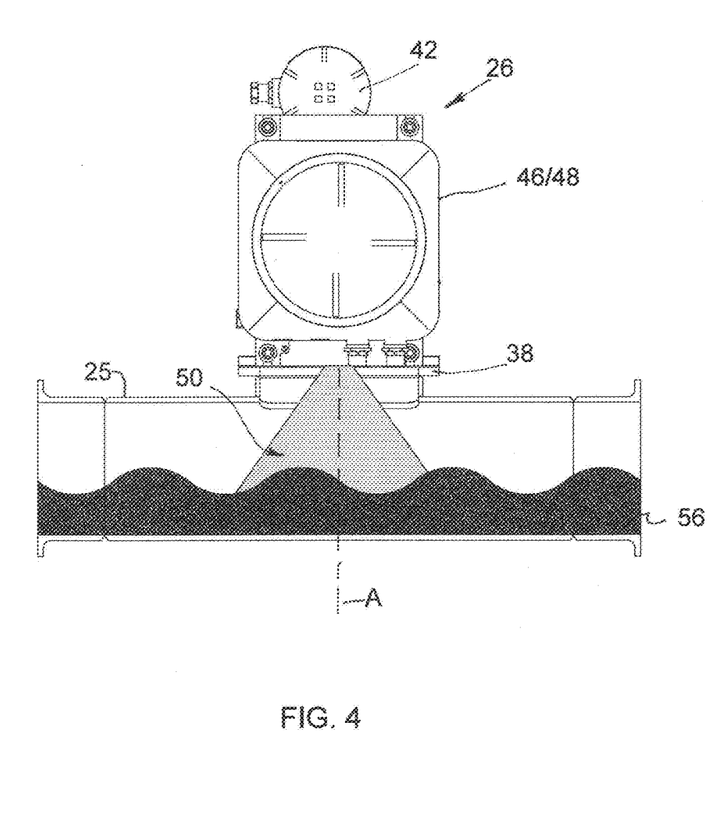
FIG. 4 is a side view of the mud flow monitoring device of FIG. 2.
Figure 5:
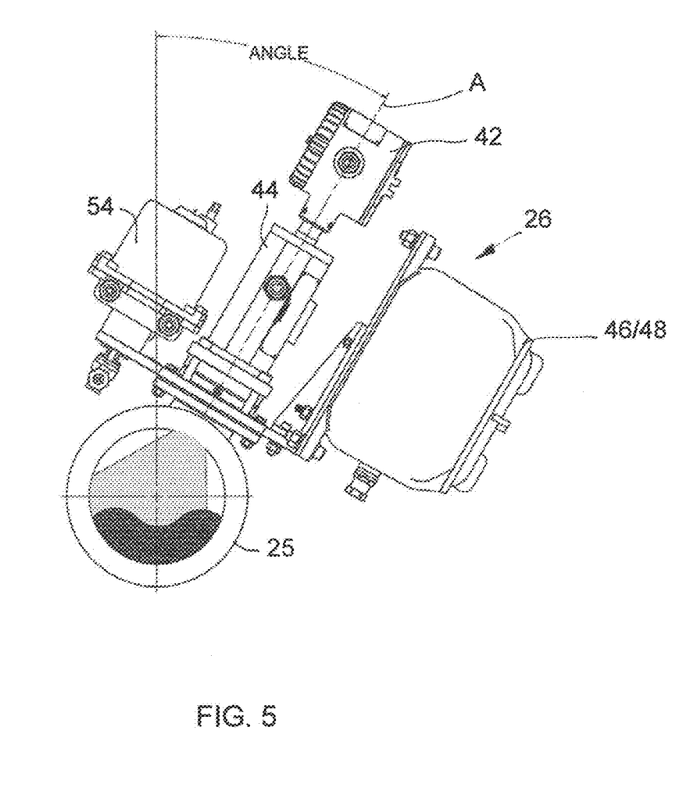
FIG. 5 is a front view of the mud flow monitoring device of FIG. 2 mounted to a pipe and offset an angle departing from a vertical orientation an amount that will be referred to as the angle of rotation.
Figure 6:
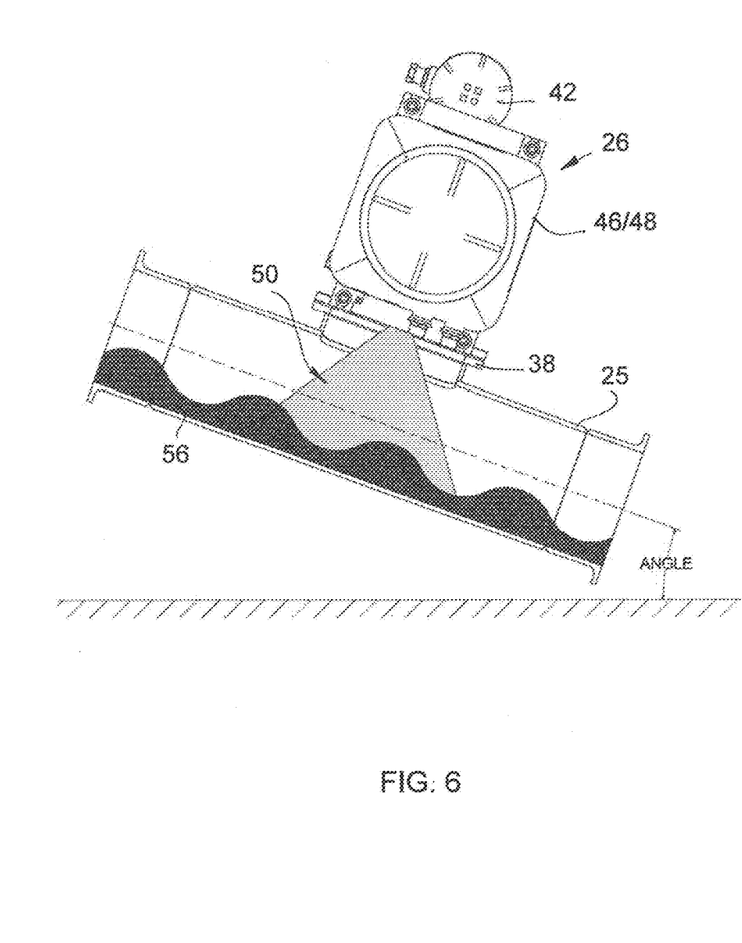
FIG. 6 is a front view of the mud flow monitoring device of FIG. 2 mounted to a pipe that is offset an angle departing from a horizontal orientation that will be referred to as the angle of tilt.

Referring to FIGS. 3 and 4, while the mud flow monitoring device 26 may be mounted such that the operational axis A of the light 43 and camera 52 is essentially vertical and mounted on a return line 25 that is oriented essentially horizontally (FIG. 3), the mud flow monitoring device 26 may be mounted to the side or flank of a return line 25 such that the axis of the light 43 and camera 52 are rotated on the return line, i.e., angled relative to a vertical orientation. This permits the mud flow monitoring device 26 to image the edge of a mud flow 56 that is higher on the sidewall of the return line 25. The axis A may be an angle of rotation from about 5 to about 55 degrees from vertical. Greater angles are also contemplated. An angle of rotation is shown in FIG. 5 with the axis A angled or offset about 30 degrees away from vertical. Accordingly, the observation zone 50 is shifted advantageously to observe a higher position along the sidewall of the pipe 25 and thus the edge of higher volume mud flows. It will be understood that the mud flow monitoring device 26 may also be mounted to a return line 25 that is inclined by, for example, about 30 degrees from horizontal. FIG. 6 illustrates the mud flow monitoring device 26 mounted to the return line 25 that has an angle of tilt of about 30 degrees.

Figure 8:
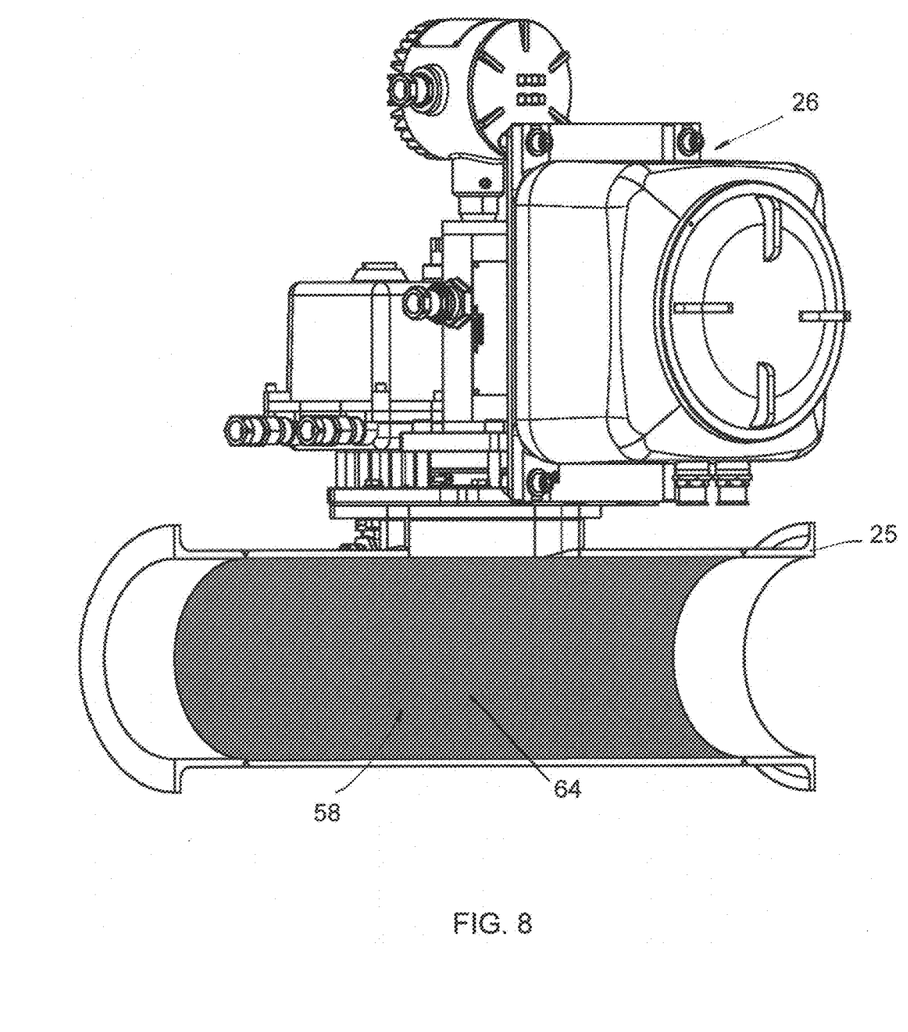
FIG. 8 is a perspective partial cutaway view of a mud flow monitoring device attached to a return line illustrating the position of a surface treatment applied to the interior of the pipe.

FIG. 8 illustrates a optional reflective or contrasting surface coating 64 that may be disposed on the interior of the return line 25 in the observation zone 50. The surface coating 64 may be configured to have a different reflectivity than the material of the mud flow and a higher contrast than that provided between a mud flow and the conventional steel material of line 25. The surface coating 64 may also be provided as one or more material with anticorrosion properties. The mud flow monitoring device 26 is thus able to detect the boundary between a mud flow in the observation zone 50 and the surface coating 64 of the pipe due to the contrast in reflectivity.

FIG. 9 illustrates an alternative or additional light 143 in the form of a laser and FIG. 11 illustrates an alternative or additional light 243 in the form of a UV lamp. The laser light 143 may be mounted to the base portion of the bracket 32 and directed light through a guide 66. The light 143 generages a beam 64 that is directed to the interior of the pipe 25 at an angle relative to the surface of the mud flow 56. The beam 64 hitting the mud flow 56 generates an illuminated spot on the surface of the mud flow that, due to the angle of the beam, has a position in the observation zone 50 that varies as a function of the level of mud flow in the pipe 25. The position of the spot is detected and analysed by the mud flow monitoring device 26 and the determined fluid level, in combination with the determined velocity of the mud flow, is used to calculate a volume flow rate. The angle of the beam is between the axial orientation of the pipe 25 and a transverse direction thereof and in the flow direction as depicted in the figure. Accordingly, a mud flow 56A that is higher in the pipe 25 would create a laser reflection spot upstream relative to a lower mud flow 56B.

The UV light 243 shown in FIG. 11 generates a beam 264 that spreads with distance like ordinary light. The UV light generated by light 243 may be used to detect oil in the mud.

Figure 10:
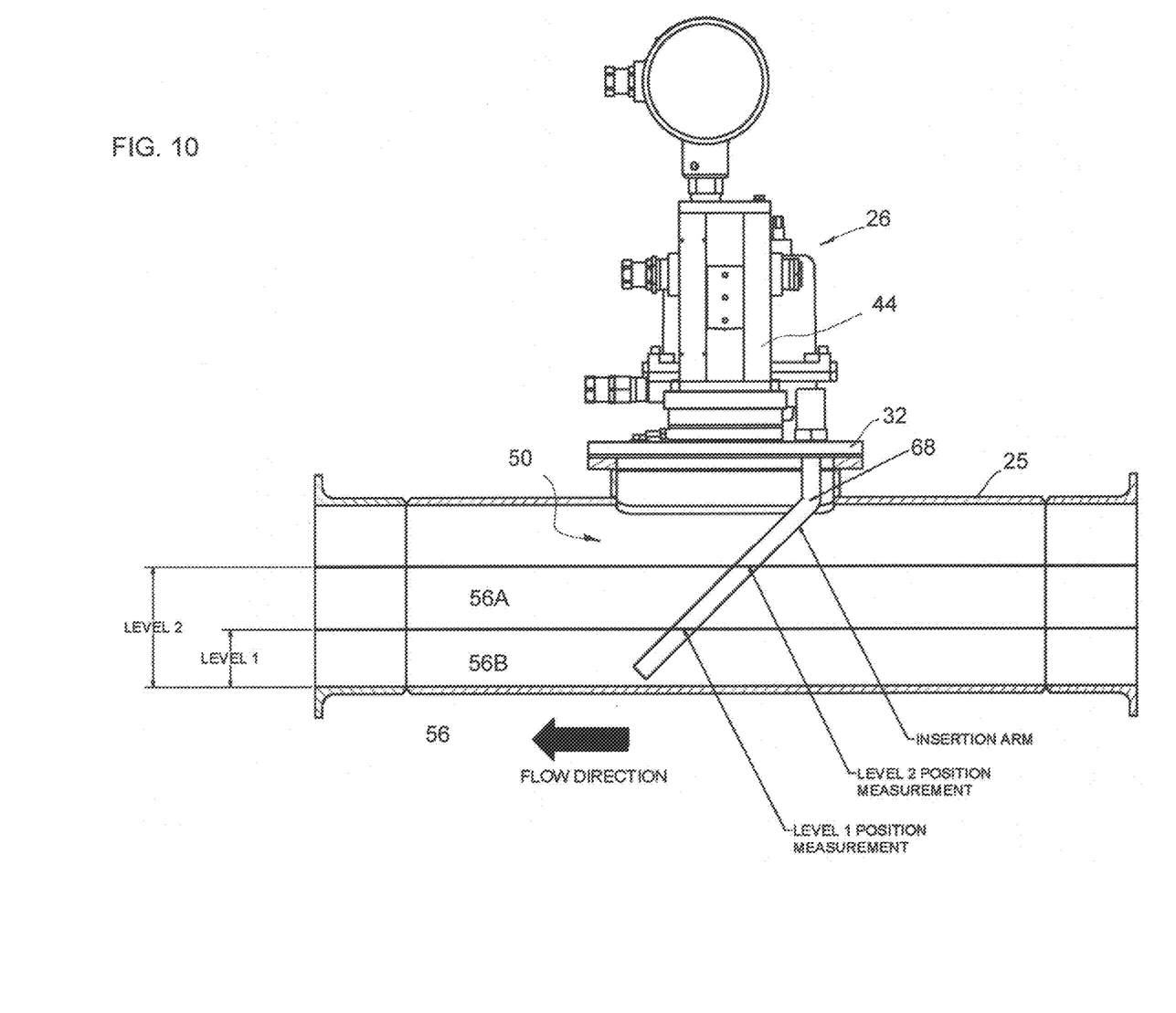
FIG. 10 is a side view of another embodiment of a mud flow monitoring device with an insertion arm.

FIG. 10 illustrates an optional insertion arm 68 that may be fixed to the bracket 32 and is configured to extend into the interior of the return line 25 in the observation zone 50. The insertion arm 68 may be a rigid or spring-biased longitudinal member that is round, oval, square, or rectangular in cross section, for example, and extends into the mud flow 56 so as to create irregularity or bubbles or the like in the surface of the mud flow. This is useful when the mud has insufficient particularity or irregularity for the camera 44 to identify and track irregularities in the mud flow and thus is unable to provide date for the calculation and determination of the velocity of mud flow. The irregularities may include differences in color, particles, bubbles, differences in reflectivity, and any other detectable noncomformity.

The insertion arm 68 therefore is configured to create such irregularities in the surface, which are detectable by the mud flow monitoring device 26. Also, when mud flow 56 fills or substantially fills the return line 25, the camera 44 may not have the ability to optically visualize the meniscus or edge of the mud flow due to the extreme angle. In such a condition, the insertion arm 68 provides a suitable mechanism to establish different level positions in a similar fashion as the laser detailed in respect to the embodiment of FIG. 9. The angle of the arm 68 is between the axial orientation of the pipe 25 and a transverse direction thereof and in the flow direction as depicted in the figure. Accordingly, a mud flow 56A that is higher in the pipe 25 would create irregularities upstream relative to a lower mud flow 56B. The insertion arm 68 may create the irregularities by simple mechanical disruption of the mud flow surface or may inject air and/or a liquid, such as water into the mud flow to provide bubbles or other types of irregularities.

Figure 12:
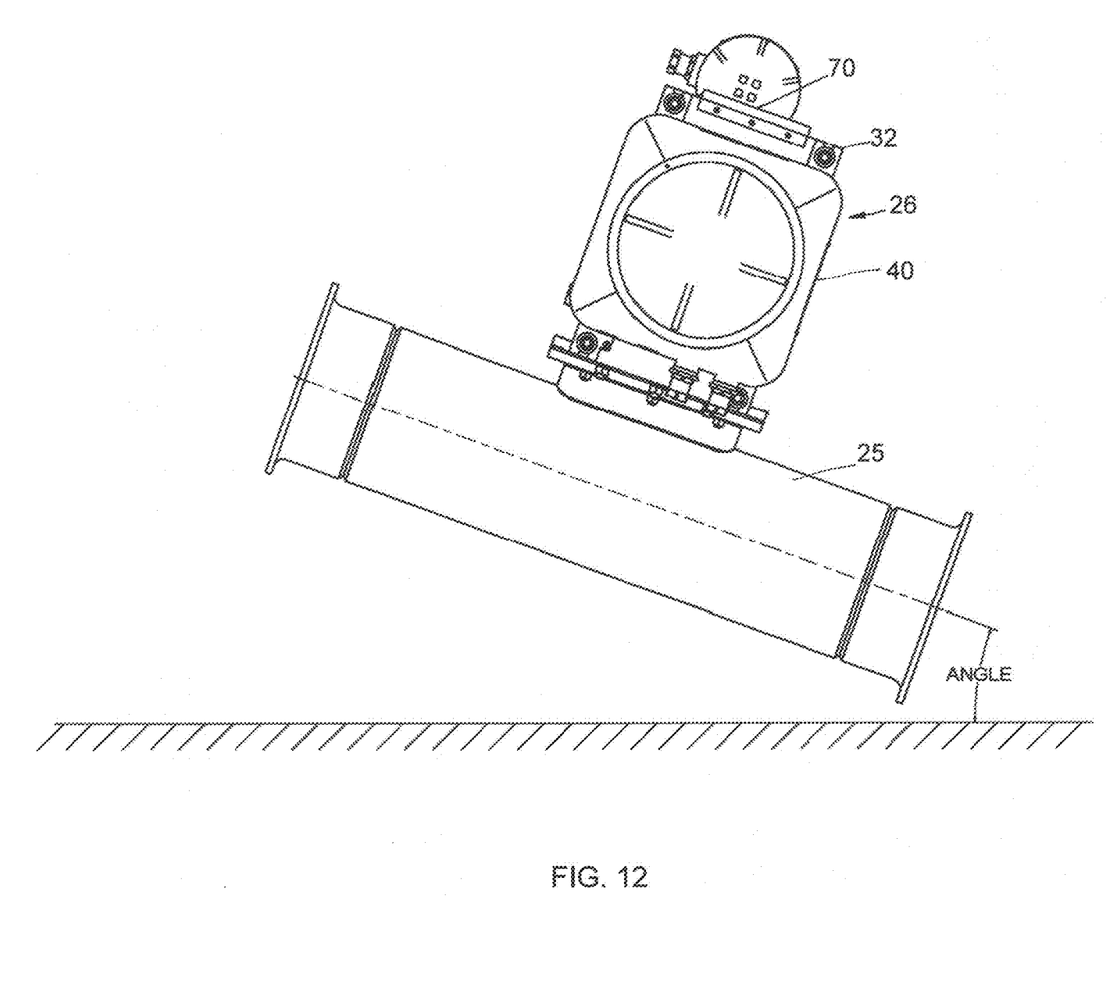
FIG. 12 is side view of yet another embodiment of a mud flow monitoring device with a reference platform for use with an angle finder to determine the operating angle of tilt and rotation of the device.

FIG. 12 illustrates a reference platform 70 for determining the incline of the mud flow monitoring device 26 and the pipe 25 to which it is attached. The reference platform 70 is affixed to the bracket 32 or housing 40 and of a size and shape that accepts an incline-determining instrument. Such instruments are common applications built into cellular phones, for example. Determining the horizontal angular incline or vertical angular offset can be used in calculating a theoretical flow rate depending on the viscosity of the mud or calibrating fluid being conveyed therethrough.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mud flow monitoring device for monitoring mud flow in a return line of a bore hole drilling operation, the flow monitoring device comprising:
    a mounting bracket mounted to the return line and having a viewing port for access to an interior of the return line;
    a light source configured to illuminate, through the viewing port, a portion of the mud flow in an observation zone within the return line, wherein the return line is provided with an inner surface that provides contrast between the mud flow and the return line;
    a camera configured to create a plurality of images of the mud flow in the observation zone; and
    a controller configured to analyze the plurality images so as to:

determine a level of the mud flow in the return line and the presence of at least one irregularity, track a movement of the irregularity across the plurality of images to determine a rate of movement of the irregularity, and calculate a flow rate of the mud flow through the return line based on the movement rate and the determined level.

2. The mud flow monitoring device of claim 1, further comprising a housing sized and shaped to enclose one or both of the light source and the camera.

3. The flow monitoring device of claim 1, wherein an operational axis of the light source and the camera are disposed at a nonvertical angle.

4. The flow monitoring device of claim 3, wherein the nonvertical angle is an angle of rotation from about 5 degrees away from vertical to about 50 degrees away from vertical.

5. The flow monitoring device of claim 1, wherein the controller is configured to control an operation of the light source.

6. The flow monitoring device of claim 5, wherein the controller is configured to coordinate operation of the light source and camera.

7. The flow monitoring device of claim 1, wherein the controller is configured to determine a level of the mud by detecting a meniscus of the mud flow, and determine an angle of the meniscus.

8. The flow monitoring device of claim 7, wherein the irregularity includes one or more of a bubble, a foam, a particle and a detectable nonconformity in the mud flow.

9. The flow monitoring device of claim 1, wherein the light source includes one or more of an LED, a laser light source, a UV light source and a light guide.

10. The flow monitoring device of claim 1, wherein the camera includes one or more of a digital still camera and a digital video camera.

11. The flow monitoring device of claim 1, further comprising a reference platform configured to receive an instrument thereupon for determining one or both of the angle of tilt and the angle of rotation.

12. The flow monitoring device of claim 1, further comprising an insertion arm for introducing into the mud flow the irregularity.

13. The flow monitoring device of claim 12, wherein the insertion arm is configured to introduce one or more of air and water into the mud flow.

14. The flow monitoring device of claim 12, wherein the insertion arm is configured to interrupt the surface of the mud flow to create the irregularity.

15. The flow monitoring device of claim 1, wherein the inner surface is of higher reflectivity relative to the mud.

16. A method of monitoring mud flow in a return line of a bore hole drilling operation, comprising:

illuminating an observation zone in the interior of the return line, wherein the return line is provided with an inner surface that provides contrast between the mud flow and the return line;

creating a plurality of images of the mud flow in the observation zone of the return line;

detecting an edge of the mud flow so as to determine a level of the mud flow in the return line;

detecting an irregularity in the mud flow and tracking movement of the irregularity over the plurality of images so as to determine a velocity of the mud flow in the return line; and calculating a volume flow rate of the mud flow based on the determined level and determined velocity.

* * * * *